United States Patent [19]

Molinoff

[11] Patent Number: 4,838,882
[45] Date of Patent: Jun. 13, 1989

[54] MOUTH MOISTURIZING PAD

[76] Inventor: Henry C. Molinoff, 234 Edgewood Ave., Smithtown, N.Y. 11787

[21] Appl. No.: 148,087

[22] Filed: Apr. 4, 1988

[51] Int. Cl.$^4$ .......................................... A61M 31/00
[52] U.S. Cl. ...................................... 604/286; 604/54; 128/859
[58] Field of Search .................... 433/168.1; 604/286, 604/304, 305, 93, 94, 48, 54, 55, 285, 904; 128/112.1, 114.1, 830, 833, 834, 839, 859, 860, 861, 832, 887, 893, 894, 899

[56] References Cited

U.S. PATENT DOCUMENTS

| | | | |
|---|---|---|---|
| D. 33,764 | 12/1900 | Georges | 128/894 |
| 335,799 | 2/1886 | Darby | 604/305 |
| 688,446 | 12/1901 | Stempel | 604/304 |
| 1,732,697 | 10/1929 | Ryan | 604/286 |
| 1,804,670 | 5/1931 | Brennan | 604/48 |
| 1,932,383 | 10/1933 | Richardson | 604/904 |
| 2,004,957 | 6/1935 | Messner | 604/93 |
| 2,081,715 | 5/1937 | Scholl | 128/894 |
| 2,098,340 | 11/1937 | Henahan | 128/859 |
| 2,146,985 | 2/1939 | Rabell | 604/904 |
| 2,178,704 | 11/1939 | Robinson | 604/904 |
| 2,286,817 | 6/1942 | Knight | 604/904 |
| 2,464,310 | 3/1949 | Harwood | 604/904 |
| 2,493,416 | 1/1950 | Negri | 604/286 |
| 2,664,631 | 1/1954 | Hollander | 433/168.1 |
| 2,725,054 | 11/1955 | Harpel | 128/163 |
| 3,055,369 | 9/1962 | Graham, Jr. | 604/904 |
| 3,150,662 | 9/1964 | Carlson, Jr. et al. | 604/55 |
| 3,226,826 | 1/1966 | Town | 433/168.1 |
| 3,397,695 | 8/1968 | Voss | 604/904 |
| 3,429,308 | 2/1969 | Russell | 604/54 |
| 3,536,074 | 10/1970 | Alfred | 604/93 |
| 3,777,754 | 12/1973 | Plachy | 604/308 |
| 3,886,935 | 6/1975 | Sprague | 128/57 |
| 4,020,844 | 5/1977 | Vickery | 604/54 |
| 4,108,180 | 8/1978 | Moehrle | 604/904 |
| 4,202,098 | 5/1980 | Russo | 433/168.1 |
| 4,239,043 | 12/1980 | Gellert | 604/372 |
| 4,341,214 | 7/1982 | Fries et al. | 604/904 |
| 4,360,013 | 11/1982 | Barrows | 604/55 |
| 4,369,773 | 1/1983 | Chuapil | 604/55 |
| 4,564,362 | 1/1986 | Burnhill | 604/55 |
| 4,624,668 | 11/1986 | Siegers | 604/904 |
| 4,678,466 | 7/1987 | Rosenwald | 604/285 |
| 4,692,143 | 9/1987 | Gero | 604/55 |

*Primary Examiner*—C. Fred Rosenbaum
*Assistant Examiner*—Sharon Rose
*Attorney, Agent, or Firm*—William G. Valance

[57] ABSTRACT

The mouth moisturizing pad for treatment of an individual suffering from xerostomia comprises at least two approximately oval shaped sponge sections saturated with water and of a size such that when placed adjacent each other the sponge sections just fit in a cheek pouch of the individual being treated and an envelope or covering made of knit cotton cloth in which the sponge sections are held. The method of treatment which is even effective during sleep thus alleviating associated frequent wakefulness comprises saturating the mouth moisturizing pad with water and inserting it in the cheek pouch of the individual where it remains because of the critically chosen dimensions.

4 Claims, 1 Drawing Sheet

4,838,882

MOUTH MOISTURIZING PAD

THE FIELD OF THE INVENTION

My invention relates to a device providing a slow release of moisture in the mouth and to a method of treatment of xerostomia or dry mouth and associated sleep disorders in elderly individuals. Reference should also be made to a copending continuation-in-part application, Mouth Moisturizing Device, submitted under separate cover by the applicant.

THE BACKGROUND OF THE INVENTION

A dry mouth is often associated with medication, particularly heart drugs. Dry mouth is often the result of oral surgery for malignancy. This is especially true when X-rays are used to treat a malignancy occurring in the mouth. It is also caused by chronic sinusitis and its attendant post-nasal drip. Furthermore it is a common complaint of no known etiology of elderly individuals.

The persistance of a dry mouth at night can disturb sleep causing the individual suffering from it to waken frequently, even every hour. Furthermore peridontal disease and increased tooth decay as well as loss of teeth can be a result of xerostomia.

Current treatment has consisted of room humidifiers, and drugs, chiefly pilocarpine. Also patients with dry mouth are advised to drink water, rinse their mouth with fluids such as mouth wash, chew gum or suck hard candy. These latter suggestions of course can only be followed when the patient is awake and are impossible to perform when asleep. Use of room humidifiers and drugs has unfortunately proven ineffective.

THE OBJECTS OF THE INVENTION

It is an object of my invention to provide an improved method for treating xerostomia or dry mouth which can act effectively even while the individual suffering from xerostomia sleeps.

It is another object of my invention to provide an improved treatment for xerostomia which does not involve use of medication which is taken internally.

It is an additional object of my invention to provide a device which is inserted in the mouth which is effective in the treatment of xerostomia even when the individual suffering from xerostomia sleeps.

It is a further object of my invention to provide a device for treating a sleep disorder including frequent nocturnal awakening which is the result of xerostomia.

SUMMARY OF THE INVENTION

According to my invention a method for treating an individual suffering from xerostomia comprises providing, advantageously saturating, a mouth moisturizing pad, which is of a size approximately equal to but not significantly less than the size of the check pouch of the individual suffering from xerostomia, with water and inserting the mouth moisturizing pad in a cheek pouch in the mouth of the individual. Advantageously the moisture content of the mouth moisturizing pad is periodically replenished as necessary by sipping water and holding the water in the vicinity of the mouth moisturizing pad in the mouth.

This treatment is completely effective providing a slow release of moisture analogous to what occurs in an uneffected individual when the tissues and glands in the mouth release saliva and moisture. Furthermore my treatment for xerostomia proceeds effectively during sleep so that the associated sleep disorder involving frequent awakening is alleviated. Thus an elderly individual who needs a good night sleep, particularly a heart patient, is provided with a means of getting that good sleep.

The mouth moisturizing pad according to my invention comprises at least two sponge sections saturated with water and positioned adjacent each other which together are approximately equal to but not significantly less than the size of the cheek pouch of the individual being treated and an envelope or covering made of cloth which covers the two sponge sections and holds them together.

Advantageously two sponge sections made of a polyester foam for durability and resiliency are used in my invention. Knit cotton cloth is used in the envelope for durability as well as comfort. Of course a poruous or water permeable covering material must be used.

The dimensions of the mouth moisturizing pad are critical since it is to be used while an individual is sleeping. It must not be too large so that it is evident by making the individual uncomfortable. On the other hand if it were too small its effectiveness would be decreased and, more importantly, it could be swallowed or inadvertently drawn in the bronchial tubes.

The mouth moisturizing pads must be made of at least two sections of polyester sponge so that the pad does not become lumpy as water is drawn from it when it is adjacent the teeth in the mouth. The outer section takes the shape of the cheek while the section lying more interiorly may be deformed. It is also desirable that their outer surfaces be somewhat convex so that they fit the shape of the cheek pouch. The use of two sections provides desirable additional comfort to the user.

BRIEF DESCRIPTION OF THE DRAWING FIGURES

SPECIFIC DESCRIPTION

Figure 1:
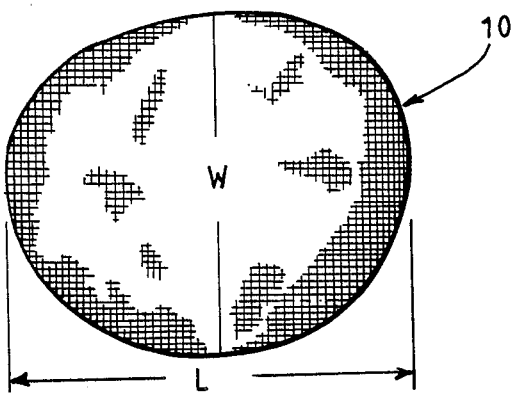
FIG. 1 is a side elevational view of a mouth moisturizing pad according to my invention.
Figure 2:
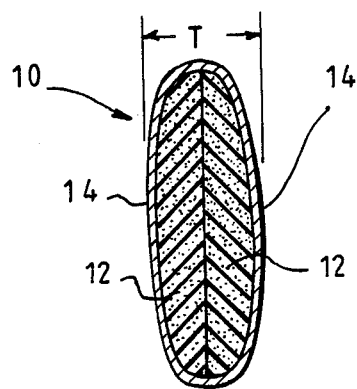
FIG. 2 is a cross sectional view of the mouth moisturizing pad of FIG. 1.
Figure 3:
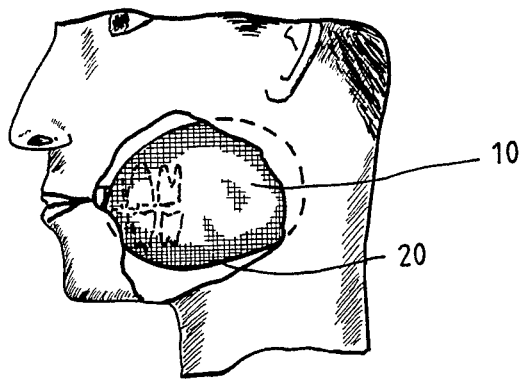
FIG. 3 is a partially cutaway side elevational view of the mouth moisturizing pad of FIG. 1 shown in place in the cheek pouch of an individual being treated.

The mouth moisturizing pad 10 shown in the drawing comprises two oval shaped polyester sponge sections 12 saturated with water and placed side by side in an envelope or covering 14 made of knit cotton cloth. The polyester sponge sections 12 are place together and knit cotton cloth pieces are placed around these sponge sections 12 and attached together, especially by sewing, to form the envelope or covering 14.

The size of the mouth moisturizing pad 10 is critical and should be about the size of the cheek pouch 20 of the individual using it, i.e. a length, l, of about 6 cm and a width, w, of about $3\frac{1}{2}$ cm varying about 1 cm from these dimensions according to the individual. It has a thickness, t, of about 2 cm. If it is too large, it is uncomfortable but if it is too small it can be swallowed or caught in the bronchial tubes or its moisture content needs to be replaced too often.

By the "cheek pouch" we mean the space between the closed teeth and the inside of the cheek.

What is claimed is new and what is desired to be protected by Letters Patent is set forth in the following claims:

1. A mouth moisturizing pad for treatment of an individual suffering from xerostomia comprising at least two sponge sections saturated with water and placed adjacent each other which are of a size such that together said sponge sections are approximately equal to but not significantly less than the size of a cheek pouch of said individual and an envelope or covering made of cloth in which said sponge sections are held.

2. A mouth moisturizing pad according to claim 1 having two of said sponge sections saturated with said water and made of polyester foam and said cloth is a knit cotton.

3. A method of treating an individual having xerostomia and associated sleep disorders comprising:
 a. providing a mouth moisturizing pad, which is of a size approximately equal to the size of a cheek pouch of said individual suffering from xerostomia, with water; and
 b. inserting said mouth moisturizing pad in said cheek pouch of said individual.

4. A method of treating an individual having xerostomia according to claim 3 further comprising periodically replenishing the moisture content of said mouth moisturizing pad as necessary by sipping a portion of said water and holding said water in the vicinity of said mouth moisturizing pad.

* * * * *